US008022257B2

(12) United States Patent
Li et al.

(10) Patent No.: US 8,022,257 B2
(45) Date of Patent: Sep. 20, 2011

(54) METHODS FOR PRODUCING POLYOLS USING CRUDE GLYCERIN

(75) Inventors: Yebo Li, Wooster, OH (US); Yuguang Zhou, Beijing (CN)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/632,433

(22) Filed: Dec. 7, 2009

(65) Prior Publication Data

US 2011/0054059 A1 Mar. 3, 2011

Related U.S. Application Data

(60) Provisional application No. 61/239,581, filed on Sep. 3, 2009.

(51) Int. Cl.
*C07C 29/00* (2006.01)
*C07C 29/128* (2006.01)
*C07C 27/00* (2006.01)
*C07C 31/00* (2006.01)
*C07C 35/00* (2006.01)

(52) U.S. Cl. .............. 568/700; 252/182.24; 568/852; 568/858; 568/868; 568/869; 568/913

(58) Field of Classification Search ............. 252/182.24; 568/700, 852, 858, 868, 869, 913
See application file for complete search history.

(56) References Cited

U.S. PATENT DOCUMENTS

| 4,742,087 | A | 5/1988 | Kluth et al. |
| 4,935,567 | A | 6/1990 | Yokoyama et al. |
| 4,987,213 | A | 1/1991 | Hirose et al. |
| 5,107,068 | A | 4/1992 | Ozaki et al. |
| 5,116,550 | A | 5/1992 | Perkins |
| 5,597,934 | A | 1/1997 | Klein et al. |
| 5,614,564 | A | 3/1997 | Hwang et al. |
| 5,908,946 | A | 6/1999 | Stern et al. |
| 5,972,057 | A | 10/1999 | Hayafuji et al. |
| 6,015,440 | A | 1/2000 | Noureddini |
| 6,025,452 | A | 2/2000 | Kurple |
| 6,184,261 | B1 | 2/2001 | Biby et al. |
| 6,284,838 | B1 | 9/2001 | Silbiger |
| 6,506,223 | B2 | 1/2003 | White |
| 6,603,048 | B1 | 8/2003 | Corbin et al. |
| 7,126,032 | B1 | 10/2006 | Aiken |
| 7,160,930 | B2 | 1/2007 | Sparks et al. |
| 7,456,229 | B2 | 11/2008 | Hager et al. |
| 7,534,923 | B2 | 5/2009 | Banavali et al. |
| 2006/0235100 | A1 | 10/2006 | Kaushiva et al. |
| 2006/0276609 | A1 | 12/2006 | Lysenko et al. |
| 2007/0232818 | A1 | 10/2007 | Crawford et al. |
| 2008/0015370 | A1 | 1/2008 | Hook et al. |
| 2008/0025903 | A1 | 1/2008 | Cortright |
| 2008/0092438 | A1 | 4/2008 | Gaus et al. |
| 2008/0249338 | A1 | 10/2008 | Rezkallah |
| 2008/0262259 | A1 | 10/2008 | Luo et al. |
| 2009/0048472 | A1 | 2/2009 | Banavali et al. |
| 2009/0069585 | A1 | 3/2009 | Halpern |
| 2009/0124719 | A1 | 5/2009 | Creazzo et al. |
| 2009/0137851 | A1 | 5/2009 | Potthast et al. |
| 2009/0143495 | A1 | 6/2009 | Nozawa et al. |
| 2009/0170974 | A1 | 7/2009 | De Schrijver et al. |
| 2009/0176904 | A1 | 7/2009 | Narine et al. |
| 2009/0275726 | A1 | 11/2009 | Krafft et al. |
| 2010/0028965 | A1 | 2/2010 | Liu et al. |
| 2010/0029799 | A1 | 2/2010 | Miyata et al. |

FOREIGN PATENT DOCUMENTS

| CN | 1869184 | 11/2006 |
| CN | 1915961 | 2/2007 |
| CN | 101314632 | 12/2008 |
| CN | 101362676 | 2/2009 |
| CN | 101362818 A | 2/2009 |
| CN | 101392054 | 3/2009 |
| CN | 101429282 | 5/2009 |
| CN | 101503338 A | 8/2009 |
| DE | 136845 A1 | 8/1979 |
| EP | 0376602 | 7/1990 |
| EP | 0518765 | 12/1992 |
| EP | 1505048 | 2/2005 |
| EP | 1772446 | 4/2007 |
| JP | 58096619 | 6/1983 |
| JP | 60177013 | 9/1985 |
| JP | 61171701 | 8/1986 |
| JP | 62079230 | 4/1987 |
| JP | 2227434 | 9/1990 |
| JP | 6172477 | 6/1994 |
| JP | 6226711 | 8/1994 |
| JP | 06263880 | 9/1994 |
| JP | 7010958 | 1/1995 |
| JP | 7011032 | 1/1995 |
| JP | 8225653 | 9/1996 |

(Continued)

OTHER PUBLICATIONS

Wang, H. et al., "A novel method of utilizing the biomass resource: rapid liquefaction of wheat straw and preparation of biodegradable polyurethane foam (PUF)," *Journal of the Chinese Institute of Chemical Engineers*, 38 (2), pp. 95-102 (Abstract, 1 page) (2007).

(Continued)

*Primary Examiner* — Rabon Sergent
(74) *Attorney, Agent, or Firm* — Thomas M. Freiburger

(57) ABSTRACT

Methods for producing a polyols and polyurethanes are described. The polyols described herein can be produced directly from crude glycerin or through liquefaction of lignocellulosic biomass using a solvent comprising crude glycerin. The polyols produced in accordance with certain aspects may be derived from a significant proportion of renewable resources.

19 Claims, 1 Drawing Sheet

FOREIGN PATENT DOCUMENTS

| | | |
|---|---|---|
| JP | 10182788 | 7/1998 |
| JP | 11130872 | 5/1999 |
| JP | 2001064351 | 3/2001 |
| JP | 2001106819 | 4/2001 |
| JP | 2002037844 | 2/2002 |
| JP | 2002037867 | 2/2002 |
| SI | 22891 A | 4/2010 |
| WO | 98/06785 | 2/1998 |
| WO | 03/029182 | 4/2003 |
| WO | 2004/011518 | 2/2004 |
| WO | 2004/011518 A2 | 2/2004 |
| WO | 2004/096882 | 11/2004 |
| WO | 2005/063840 | 7/2005 |
| WO | 2008/049097 | 4/2008 |
| WO | 2008/053780 | 5/2008 |
| WO | 2009/131141 | 10/2009 |
| WO | WO2010020903 A1 | 2/2010 |

OTHER PUBLICATIONS

Wang, Y. et al., "Liquefaction of corn stover using industrial biodiesel glycerol," *Int. J. Agric. & Biol. Eng.*, vol. 2, No. 2, pp. 32-40 (Jun. 2009).

Chen, F. et al., Liquefaction of Wheat Straw and Preparation of Rigid Polyurethane Foam from the Liquefaction Products, *Journal of Applied Polymer Science*, vol. 111, pp. 508-516 (2009).

Crooks, A., "Evolving technology may generate profit from biodiesel glycerin glut," *Rural Cooperatives*, pp. 30-32, 37 (Jul./Aug. 2007)

Kiatsimkul, P. et al., "Preparation of high hydroxyl equivalent weight polyols from vegetable oils," *Industrial Crops and Products*, 27, pp. 257-264 (2008).

Kiatsimkul, P. et al., "Production of new soy-based polyols by enzyme hydrolysis of bodies soybean oil," *Industrial Crops and Products*, 25, pp. 202-209 (2007).

Liang, L. et al., "Liquefaction of Crop Residues for Polyol Production," *BioResources*, 9 pages (2006).

Lu, J. et al., "Additive toughening effects on new bio-based thermosetting resins from plant oils," *Composites Science and Technology*, 68, pp. 1025-1033 (2008).

Lubguban, A. A. et al., "Functionalization via Glycerol Transesterification of Polymerized Soybean Oil," *Journal of Applied Polymer Science*, vol. 112, pp. 19-27 (2009).

Mielewski, D.F. et al., "Soybean oil auto applications," *Industrial Biotechnology*, pp. 32-34 (Spring, 2005).

Melero, J. A. et al., "Biodiesel Production with Heterogeneous Sulfonic Acid-Functionalized Mesostructured Catalysts," *Energy & Fuels*, 23, pp. 539-547 (2009).

Nilles, D., "Combating the Glycerin Glut," *Biodiesel Magazine*, 3 pages (Sep. 2006).

Petrović, Z.S., "Polyurethanes from Vegetable Oils," *Polymer Reviews*, 48, pp. 109-155 (2008).

Tu, Y. et al., "Physical Properties of Water-Blown Rigid Polyurethane Foams from Vegetable Oil-Based Polyols," *Journal of Applied Polymer Science*, vol. 105, pp. 453-459 (2007).

Voegele, E., "Glycerin: Research Turns Up New Uses," *Biodiesel Magazine*, 2 pages (Mar. 2009).

Wang, T. et al., "Effects of CS/EC ratio on structure and properties of polyurethane foams prepared from untreated liquefied corn stover with PAPI," *Chemical Engineering Research and Design*, 86, pp. 416-421 (2008).

Wang, T. et al., "Mechanical properties of polyurethane foams prepared from liquefied corn stover with PAPI," *Bioresource Technology*, 99, pp. 2265-2268 (2008).

Yu, F. et al., "Atmospheric Pressure Liquefaction of Dried Distillers Grains (DDG) and Making Polyurethane Foams from Liquefied DDG," *Appl. Biochem. Biotechnol.*, 148, pp. 235-243 (2008).

Zeman, N., "The Poly-Refinery Plan," *Biodiesel Magazine*, 2 pages (Mar. 2007).

Zhang, T. et al., "Qualitative analysis of products formed during the acid catalyzed liquefaction of bagasse in ethylene glycol," *Bioresource Technology*, 98, pp. 1454-1459 (2007).

Chen, F. et al., "Preparation of rigid polyurethane foam from liquefied wheat straw," *Research Progress in Pulping and Papermaking*, [International Symposium on Emerging Technologies of Pulping and Papermaking], 3rd, Guangzhou, China, (Nov. 8-10, 2006), 873-878 (Abstract; 1 page).

Kunaver, M. et al., "Liquefaction of wood, synthesis and characterization of liquefied wood polyester derivatives," *Journal of Applied Polymer Science* (2010), 115(3), 1265-1271 (Abstract; 1 page).

Kurimoto, Y. et al., "Recycling of waste wooden construction materials using wood-liquefaction system and steam-injection molding system," *Mokuzai Kogyo* (2005), 60(2), 70-74 (Abstract; 1 page).

Liu, Y. et al., "Preparation of biopolymers from liquefied corn stover," *Nongye Gongcheng Xuebao* (2005), 21(12), 116-120 (Abstract; 1 page).

Wang, H. et al., "A novel method of utilizing the biomass resource: rapid liquefaction of wheat straw and preparation of biodegradable polyurethane foam (PUF)," *Journal of the Chinese Institute of Chemical Engineers* (2007), 38(2), 95-102 (Abstract, 1 page).

Yan, Y. et al., "Preparation and characterization of water-blown polyurethane foams from liquefied cornstalk polyol," *Journal of Applied Polymer Science* (2008), 110(2), 1099-1111 (Abstract; 1 page).

Kapila, S. et al, "Synthesis and Characterisation of Soyhull Glycerol Derived Rigid Polyurethane Foams", Society for the Advancement of Material and Process Engineering (SAMPE) Conference Proceedings, 2004, No. 49.

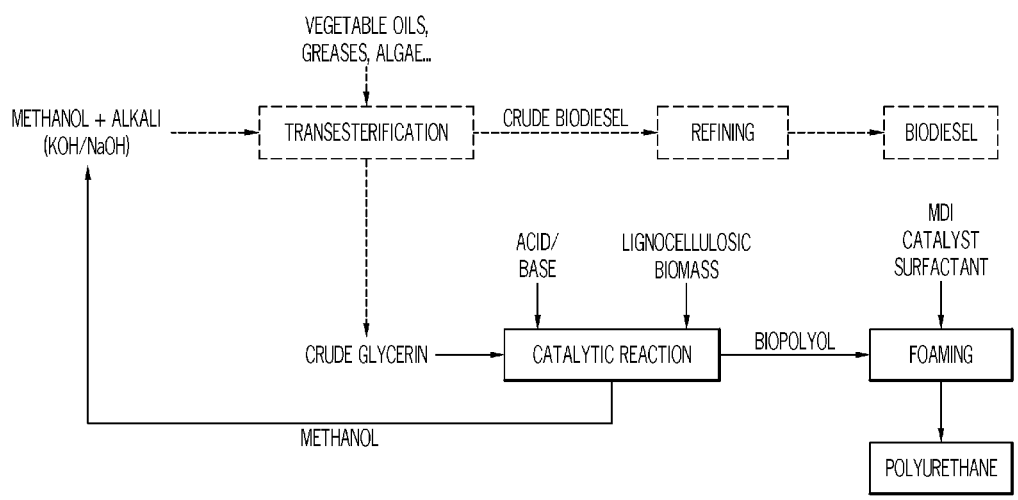

METHODS FOR PRODUCING POLYOLS USING CRUDE GLYCERIN

CROSS REFERENCE TO RELATED APPLICATION

This application claims the benefit of U.S. Application Ser. No. 61/239,581 filed Sep. 3, 2009, the contents of which are hereby incorporated by reference.

BACKGROUND

The present application relates to methods for producing polyols and polyurethanes, and more particularly, to producing polyols from lignocellulosic biomass using a solvent containing crude glycerin. The resulting polyols can be used as starting materials for various products and in particular the polyols can be used to produce polyurethanes.

The industrial manufacturing of polyurethane foam and elastomer products relies significantly on fossil fuels and their derivatives as major reactants for the production of polyols. Certain aspects of the present application are directed to methods of manufacturing polyurethanes using materials that are in abundant supply and obtained from renewable resources. By utilizing renewable resources instead of relying on limited supplies of fossil fuels and derivatives, some aspects of the present invention provide methods for manufacturing polyurethane products through an environmentally friendly process that is also characterized by reduced production costs because the raw materials are readily available byproducts or waste products.

The major global consumption of polyurethane products is in the form of foams which come in two types, flexible and rigid, being roughly equal in market size. In 2007, the global consumption of polyurethane (PU) raw materials was above 12 million metric tons; the average annual growth rate is about 5%. Polyurethane products are used in many different ways as summarized in Table 1 below.

TABLE 1

Polyurethane products consumption (US Data 2004)

| Application | Amount of polyurethane used (millions of pounds) | Percentage of total |
| --- | --- | --- |
| Building & Construction | 1,459 | 26.80% |
| Transportation | 1,298 | 23.80% |
| Furniture & Bedding | 1,127 | 20.70% |
| Appliances | 278 | 5.10% |
| Packaging | 251 | 4.60% |
| Textiles, Fibers & Apparel | 181 | 3.30% |
| Machinery & Foundry | 178 | 3.30% |
| Electronics | 75 | 1.40% |
| Footwear | 39 | 0.70% |
| Other uses | 558 | 10.20% |
| Total | 5,444 | 100.00% |

The general polyurethane polymer-forming reaction between an isocyanate as the A-side component and an alcohol or polyol as the B-side component is as follows:

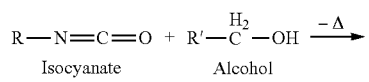

Isocyanate    Alcohol

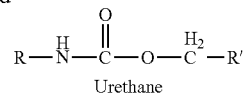
Urethane

Typical Reaction of Urethane Formation.

One source of crude glycerin is as a byproduct and waste from the transesterification process of biodiesel production. Biodiesel, produced according to ASTM D 6751, is known as a mono-alkyl methyl ester (fatty acid methyl ester, FAME) or methyl ester for short. It can be made from multiple sources (waste vegetable oil, soybean oil, canola oil, sunflower oil, corn oil, flaxseed oil, cottonseed oil, peanut oil, lard, grease, poultry fat, cooking oil, algae etc.). Crude glycerin derived from biodiesel production has very low value because of its impurities. Generally, crude glycerin appears as a brown liquid since it contains glycerin, methanol, sodium hydroxide, moisture, and some fat residues.

SUMMARY

The present application is directed to methods for producing polyols from crude glycerin. In accordance with one aspect, polyols can be produced from crude glycerin itself. In accordance with another aspect, polyols can be produced through the liquefaction of lignocellulosic biomass using a solvent comprising crude glycerin. In accordance with one aspect, lignocellulosic biomass is combined with crude glycerin to form an admixture and the admixture is heated to liquefy the biomass and produce a polyol.

In accordance with other embodiments, the polyol produced from the liquefied lignocellulosic biomass or the polyol produced from crude glycerin itself can be used as a reactant in a method for producing polyurethane.

The present application is also directed to the polyols and polyurethanes produced in accordance with the described methods.

BRIEF DESCRIPTION OF THE DRAWING

The FIGURE is a schematic diagram illustrating one embodiment of the present invention related to the production of biopolyols and polyurethanes from the crude glycerin byproduct of the biodiesel production process.

DETAILED DESCRIPTION

The present application is directed to methods for producing polyols utilizing crude glycerin. Polyols can be produced directly from the crude glycerin or through liquefaction of lignocellulosic biomass using a solvent comprising crude glycerin. In accordance with certain aspects of the present invention, polyols are produced in accordance with methods that utilize non-petroleum and non-food feedstock, some of which are considered waste byproducts. Polyols produced in accordance with the methods described herein can be considered highly functional polyols that can be used as a reactant in various reactions, including as a reactant in a method for producing polyurethane. In accordance with some aspects, the resulting polyols can be used directly for producing polymers. Isolation or purification of the polyols is not required.

Biomass, a renewable energy source, is biological material derived from living, or recently living organisms. It also includes lignocellulosic plant materials such as corn stover, wheat bran, rice stalk, soybean straw, herbals and wood sawdust.

In accordance with one embodiment, lignocellulosic biomass is used as one part of the raw material for liquefaction as described herein. Generally, lignocellulosic biomass refers to agricultural wastes (corn stover, wheat straw, rice stalk, soybean straw, etc.), wood wastes (dead trees, wood chips, sawdust, etc.), and other types of plants, industrial paper pulp, herbals and so on.

The lignocellulosic biomass material typically is reduced in size to facilitate liquefaction. In accordance with certain aspects, the material can be chopped into pieces. It can also be milled to provide the appropriate size particles. The liquefaction process in accordance with certain embodiments utilizes biomass particles below about 50 mm, more particularly below about 20 mm.

In accordance with one aspect, crude glycerin obtained as a byproduct of biodiesel production is used as solvent in the liquefaction process described herein. Crude glycerin typically contains glycerin, methanol, inorganic salts such as sodium hydroxide or potassium hydroxide, water, oils or fat, soap, and so on. As used herein, "crude glycerin" refers to a glycerin product that is obtained as a by-product of a reaction and, in particular, as a by-product of a reaction for producing biodiesel fuel (BDF). Crude glycerin is produced during the production of BDF typically has a glycerin content of about 40-88% and can be partially refined to remove or reduce impurities such as methanol, water, salts and soaps. Partial refinement can increase the glycerin content up to about 90% glycerin, more particularly up to about 95% glycerin and in certain cases up to about 97% glycerin, approaching the purity associated with technical grade glycerin. As used herein, crude glycerin includes crude glycerin as produced and crude glycerin that has been partially refined to a purity near that for technical grade glycerin. The term "unrefined crude glycerin" refers to crude glycerin as produced during a reaction such as BDF production in which the byproduct has not been refined other than being treated to remove methanol and large impurities such as the fat and soap layer. Crude glycerin from a particular biodiesel production process utilizing NaOH as a catalyst was analyzed to determine levels of other elements/metals. Na was found to be of highest concentration (18,300 ug/g average). Other metals of relatively higher concentration include K (79 ug/g average, Ca (18 ug/g average, Mg (5.2 ug/g average). Other metals/elements were present in trace amounts. The glycerin by-product from the NaOH catalyzed biodiesel process may contain at least 5000 ug/g, more particularly at least 10,000 ug/g, and in certain cases at least 15,000 ug/g sodium.

As used herein, the terms "glycerin," "glycerine," or "glycerol" are used interchangeably and refer to the compound 1,2,3, propanetriol. The terms "biopolyol" and "bio-based polyol" refer to polyols synthesized from bio-based materials such as agricultural biomass, vegetable oils or animal fats. Polyols produced in accordance with certain embodiments may be derived from at least 70%, more particularly at least 80%, and in some cases at least 90% from renewable resources. In still other cases the polyols may be derived from substantially all renewable resources. The term "substantially" allows for small amounts (<1-2%) of non-renewable materials.

Although the economic benefits of certain aspects of the present invention are related to the use of low-cost crude glycerin, some portion of the solvent mixture can include refined (>97% purity) glycerin or other solvents. In accordance with certain embodiments, the amount of refined glycerin or other solvent would be no more than 50%, more particularly no more than 20%, no more than 10% or no more than 5%, by weight of the total solvent by weight. In accordance with other embodiments, the solvent comprises substantially 100% crude glycerin. The term "substantially" allows for trace amounts (less than 2%) of other solvents or components besides the crude glycerin. In accordance with still other embodiments, the solvent consists essentially of crude glycerin product as obtained from the generating source.

The reaction for producing BDF may include a transesterification reaction or alcoholysis reaction that occurs in a basic reaction mixture (e.g., having a pH greater than about 11) comprising triglycerides (e.g., which are present in animal or vegetable fats or oils) and alcohol (e.g., methanol or ethanol). The reaction mixture may produce fatty acid alkyl esters (e.g., fatty acid methyl esters) and glycerin.

As indicated above, the fat and soap layer from the crude glycerin may be skimmed to get rid of floating impurities. The main liquefaction process can be performed in either pressurized or atmospheric conditions. Biomass and solvent, primarily crude glycerin, are well mixed in a biomass to solvent mass ratio range sufficient to effectively liquefy the biomass. Typically, the ratio of biomass to solvent mass is about 0.05-20%, more specifically about 0.5-15%, and in certain cases about 5-10%. The ratio is expressed as a percentage equivalent to the mass of biomass divided by the mass of solvent.

In accordance with certain embodiments, polyols can also be produced from crude glycerin in the absence of separately provided biomass. Polyols produced directly from crude glycerin can also be used to produce polyurethanes in accordance with certain aspects of the present invention. The process for producing polyols from crude glycerin without biomass is essentially the same as the process described herein relating to liquefaction of biomass in a solvent containing crude glycerin.

The liquefaction process typically is conducted at an elevated temperature for an amount of time effective to produce the polyol from the biomass and solvent. Typical reaction conditions include temperatures of 130° C. to 220° C. for about 10 minutes to about 10 hours. In accordance with certain embodiments, the reaction may be conducted in a temperature range of about 180° C. to 215° C., more particularly about 185 to 210° C. and in accordance with certain embodiments about 190-200° C.

A catalyst (acid, base, or salt) may also be used and can be processed with or without continuous blending. Examples of catalysts that may be used include, without limitation, $H_2SO_4$, $CH_3COOK$, HCl, $H_3PO_4$, HCOOH, $ZnCl_2$, NaOH, KOH, $Na_2CO_3$, $K_2CO_3$, $Rb_2CO_3$, $Cs_2CO_3$, Ni, $Cu(OH)_2$, $NaHCO_3$, NaAc, MgAc, $NH_4Cl$, $ZnCl_2$, $AlCl_3$, $(NH_4)_2SO_4$, $FeSO_4$, $Fe(NH_4)(SO_4)_2$, $ZnSO_4$, $CaSO_4$, $MgSO_4$, $NaH_2PO_4$, $Na_2HPO_4$, Ni, etc. Typically, catalysts may be used at a concentration of about 0.5-10%, more particularly about 1-5%. When concentrated sulfuric acid is used, the sulfuric acid concentration may be about 2-6%.

The liquefaction process is continued for a time sufficient to sufficiently convert the lignocellulosic biomass to a polyol composition. In certain conditions, the liquefaction lasted for less than 90 minutes. Typically, a black-colored, semi-fluid product is obtained after liquefaction.

In accordance with certain aspects of the present invention, the liquefaction process results in a biomass conversion of at least 70%, more particularly at least 80%, still more particularly at least 90% and in some cases at least 95%. The percent conversion quantifies the amount of insoluble residue remaining after the liquefaction process. The percent conversion can be measured by dissolving a weighed sample of the polyol product in a 4:1 v/v dioxane-water solution and letting the dissolved sample stand for 24 hours without stirring. After standing, the solvent is filtered out and the sample is washed with solvent until clear. The insoluble material on the filter paper is dried overnight in an oven at 105° C. and then weighed. The % conversion can be calculated using the following equation:

% conversion=$[1-(Wr/Ws)] \times 100$ where Ws is the weight of the initial sample and Wr is the weight of the insoluble residue.

In accordance with a particular embodiment, the liquefaction set-up includes a three-necked round-bottom flask connected to a reflux condenser. A 500-mL three-necked round-bottom flask fitted with a reflux condenser, a heater, thermometer, and mechanical stirrer is set up under a fume hood. The pre-weighed lignocellulosic biomass, crude glycerin, and catalyst are added into the flask and heated to an elevated temperature. The reflux condenser is provided with a gas port connected to a rubber tubing into a bottle where the condensing methanol-rich steam is collected. Methanol can be recovered through the reflux condenser at temperatures up to 130° C. The recovery ratio of methanol is dependent on the methanol content of the crude glycerin, which typically is in the range of about 1020% but can vary depending on the biodiesel process and the starting materials.

The liquefied biomass-based polyol (biopolyol) can be used for polyurethane production. Polyurethanes are formed from the general reaction of an isocyanate (A-side) and an alcohol component (B-side) to form the urethane monomer that makes up the polyurethane polymer network. The isocyanate is a compound that provides the source of —NCO groups to react with functional groups from the polyol, water, and cross-linkers in the formulation.

Polyurethane foams can be produced by reacting a polyol composition with an isocyanate such as diphenylmethane diisocyanate according to known methodology. Typically, the polyol composition, a blowing agent (to form bubbles), a catalyst, and a surfactant are mixed together before adding the isocyanate. Reaction conditions can be adjusted to control the type of polyurethane that is produced (e.g., flexible, semi-rigid, or rigid polyurethane foam). Polyurethane foams produced with the polyol compositions can be used as packaging, construction and insulating materials, and can be formulated to be biodegradable.

Isocyanates which may be used in the present invention include aliphatic, cycloaliphatic, arylaliphatic and aromatic isocyanates. Examples of suitable aromatic isocyanates include the 4,4'-, 2,4' and 2,2'-isomers of diphenylmethane diisocynate (MDI), blends thereof and polymeric and monomeric MDI blends, toluene-2,4- and 2,6-diisocyanates (TDI), m- and p-phenylenediisocyanate, chlorophenylene-2,4-diisocyanate, diphenylene-4,4'-diisocyanate, 4,4'-diisocyanate-3,3'-dimethyldiphenyl, 3-methyldiphenyl-methane-4,4'-diisocyanate and diphenyletherdiisocyanate and 2,4,6-triisocyanatotoluene and 2,4,4'-triisocyanatodiphenylether.

Mixtures of isocyanates may be used, such as the commercially available mixtures of 2,4- and 2,6-isomers of toluene diisocyanates. A crude polyisocyanate may also be used in the practice of this invention, such as crude toluene diisocyanate obtained by the phosgenation of a mixture of toluene diamine or the crude diphenylmethane diisocyanate obtained by the phosgenation of crude methylene diphenylamine. TDI/MDI blends may also be used.

Examples of aliphatic polyisocyanates include ethylene diisocyanate, 1,6-hexamethylene diisocyanate, isophorone diisocyanate, cyclohexane 1,4-diisocyanate, 4,4'-dicyclohexylmethane diisocyanate, saturated analogues of the above mentioned aromatic isocyanates and mixtures thereof.

For the production of flexible foams, polyisocyanates that are particularly useful include toluene-2,4- and 2,6-diisocyanates or MDI or combinations of TDI/MDI or prepolymers made therefrom.

Isocyanates useful herein typically contain at least two isocyanate groups per molecule. The Dow Chemical Company offers a broad range of isocyanates which include ISONATE® MDI (methylene diphenyl diisocyanate) and PAPI® polymeric MDI for polyurethane processing and solution applications in coatings, adhesives, sealants and elastomers. For example, PAPI® 27 is a polymeric MDI with a 31.4% weight NCO, 134 isocyanate equivalent weight, >204° C. flash point, and 180 cSt viscosity at 25° C.

In polyurethane chemistry, the isocyanate index is the amount of isocyanate used relative to the theoretical equivalent amount, i.e., 100 times the ratio of NCO groups to reactive hydrogen of the polyol composition and the reaction mixture. The isocyanate index typically ranges from about 5 to about 150, more particularly from about 10 to about 110 and in accordance with certain embodiments from about 10 to about 80.

One or more crosslinkers may be present in the foam formulation. If used, suitable amounts of crosslinkers are from about 0.1 to about 1 part by weight, especially from about 0.25 to about 0.5 part by weight, per 100 parts by weight of polyols.

As used herein, "crosslinkers" are materials having three or more isocyanate-reactive groups per molecule and an equivalent weight per isocyanate-reactive group of less than 400. In accordance with some aspects, crosslinkers contain from 3-8, especially from 3-4 hydroxyl, primary amine or secondary amine groups per molecule and have an equivalent weight of from 30 to about 200, especially from 50-125. Examples of suitable crosslinkers include diethanol amine, monoethanol amine, triethanol amine, mono-di- or tri(isopropanol) amine, glycerine, trimethylol propane, pentaerythritol, sorbitol and the like.

It is also possible to use one or more chain extenders in the foam formulation. As used herein, a chain extender is a material having two isocyanate-reactive groups per molecule and an equivalent weight per isocyanate-reactive group of less than 400, especially from 31-125. The isocyanate reactive groups are preferably hydroxyl, primary aliphatic or aromatic amine or secondary aliphatic or aromatic amine groups. Representative chain extenders include amines ethylene glycol, diethylene glycol, 1,2-propylene glycol, dipropylene glycol, tripropylene glycol, ethylene diamine, phenylene diamine, bis(3-chloro-4-aminophenyl)methane and 2,4-diamino-3,5-diethyl toluene. If used, chain extenders are typically present in an amount from about 1 to about 50, especially about 3 to about 25 parts by weight per 100 parts by weight high equivalent weight polyol, the contents of which are hereby incorporated by reference.

The use of such crosslinkers and chain extenders is known in the art as disclosed in U.S. Pat. No. 4,863,979 and EP Publication 0 549 120, the contents of which are hereby incorporated by reference.

Any commercial blowing agent or method to cause expansion of the material can be used in forming the foam of the present invention. Examples of blowing agents that may be used include, but are not limited to, water, carbon dioxide, and pentane. The blowing agent functions to expand the product and turn it into a foam.

Water is a particularly useful blowing agent for formulations of the present invention. In formulations useful for preparing the polyurethane foams of the present invention, water may be present at a concentration of from about 0.75 to 6 weight percentage of biopolyols. In accordance with certain embodiments, water may be present at from about 1.0 to 6.0 weight percentage of B-side component. In accordance with other embodiments, water may be present at from about 2.0 to 4.0 weight percentage of B-side component.

While some polyurethane foam formulations may include water as the only blowing agent, it is also contemplated that the present invention includes formulations having minor amounts of auxiliary blowing agents as well. When an auxiliary blowing agent is used, it may be present between about 0.01 to 10 weight percentage of the B-side component. More particularly, the auxiliary blowing agent may be present between about 0.1 to 5 weight percentage. For example, both water and one or more of the following materials could be used as blowing agents for the formulations of the present invention: HCFC-22, HFC-134a, HCFC-142b, HFC-245fa, dichloroethylene, hydrocarbons such as n-pentane, isopentane, cyclopentane and the like. Small amounts of such auxiliary blowing agents when used with the composition of the present invention may result in higher insulation values. In accordance with other aspects, a blowing agent can be used that does not contain water.

The B-side component may include some metal salt catalyst. The metal salt catalysts, along with the excess heat of reaction, causes the residual isocyanate to react with itself to form very stable isocyanurate functionality. The metal salt catalysts are alkali metal salts of organic acids, more particularly sodium or potassium salts. Metal salt catalyst may be present between about 0.05 to 10 weight percent. Examples of commercially available metal salt catalyst suitable for the present invention include DABCO® K-15 and Polycat® 46 from Air Products, and the like. Other common catalysts used for flexible foam formulation include Stannous octoate and Dibutyltin dilaurate—both tin-based.

In addition to the above referenced components, the B-side component may also include additional catalysts, surfactants, flame retardants or other additives such as would be known to those of skill in the art. The B-side component may include at least one amine catalyst. Commercially available amine catalysts suitable for the present invention include Polycat® 5, Polycat® 8, Polycat® 11, DABCO® 33 LV, DABCO® BL-17 and DABCO® BL-11 from Air Products. Other amine catalysts can also be used. In accordance with certain embodiments, the amine catalyst may be present in an amount between about 0.1 and about 4.0 weight percentage of the B-side component.

Surfactants may be present in an amount between about 0.25 and about 3.0 weight percentage of the B-side component. These surfactants typically take the form of polydimethylsiloxane-polyoxyalkylene block copolymers, silicone oils, nonylphenol ethoxylates, and other organic compounds. Commercially available surfactants suitable for the present invention include DABCO® DC5357, DABCO® DC2585, DABCO® DC193, DABCO® DC4053, DABCO® DC5098 from Air Products, and the like.

Additionally, flame retardants can be used in the B-side component of the present invention. In accordance with some embodiments, between about 5.0 and about 15 weight percentage flame retardant may be used. Frequently used flame retardants include tris(chloroethyl)phosphate, tris(chloroisopropyl)phosphate and tris(dichloroisopropyl) phosphate. U.S. Pat. No. 3,830,890 describes tetra esters of 2-butene-1,4-diphosphonic acid as flame retardants for polyurethane foams. U.S. Pat. No. 4,067,931 describes tetraalkyl esters of polyoxymethylenediphosphonic acid as flame retardants for polyurethane foams. Other flame retardant chemicals used in polyurethane foams include triphenyl phosphate, chloroalkyl phosphate, aryl phosphates and other organic phosphate esters.

The A:B volume ratio typically is between about 1:1 and about 3:1. More particularly, the A:B volume ratio typically is between about 1.2:1 and about 2.5:1. Even more particularly, the A:B volume ratio typically is between about 1.25:1 and about 2.0:1. In accordance with particular embodiments, the A:B volume ratio may be about 1.5:1.

Processes for producing polyurethane products from the polyols described herein are not particularly limited, and any of the processes known in the art can be used. Typically, the components of the polyurethane-forming reaction mixture may be mixed together in any convenient manner, for example, by using any of the mixing equipment described in the prior art for the purpose such as described in "Polyurethane Handbook," by G. Oertel, Hanser publisher. The polyurethane products may be produced either continuously or discontinuously, by injection, pouring, spraying, casting, calendering, etc. Polyurethane products may be produced under free rise or molded conditions, with or without release agents, etc.

Rigid foams may be produced using the known 1-shot prepolymer or semi-prepolymer techniques, together with conventional mixing methods including impingement mixing. The rigid foam may also be produced in the form of slabstock, moldings, cavity filing, sprayed foam, frothed foam or laminates with other materials such as paper, metal, plastics or wood-board. Flexible foams may be either free rise or molded while microcellular elastomers are usually molded.

Polyurethane foam produced in accordance with certain aspects of the present invention can be applied to a surface or substrate by reacting the A-side component and the B-side component to form a polyurethane reaction product and applying the polyurethane reaction product to the surface or substrate. Examples of surfaces to which the polyurethane foam can be applied include, without limitation, roofs, structural walls, exterior surfaces, interior surfaces, storage tanks, insulated cavities, and process vessels.

Several important properties of the biopolyol dictate polyurethane formulation. These physicochemical properties include acid number, hydroxyl number and viscosity. Acid and hydroxyl numbers are needed to calculate the amount of isocyanate needed for urethane reaction. Acid number (mg KOH/g) is defined as the amount in milligrams of potassium hydroxide required to neutralize the acid present in one gram of a polyol sample (usually present as acid residuals in the polyol). Typical values of acid number in commercially-available polyols are less than 10 mg KOH/g sample. Low acidity in some polyols can be important because high acid number polyols tend to neutralize the urethane formulation catalysts and react with isocyanate to compete with hydroxyls in the urethane formation. In accordance with certain aspects, the measured acid numbers of the produced biopolyols range from about 2-50 mg KOH/g.

Hydroxyl Number is an index of the amount of reactive hydroxyl groups available for reaction. This value is determined using a wet analytical method and is reported as mg KOH/g sample (amount in milligrams of KOH equivalent to the hydroxyl groups found in a gram of a polyol sample). Rigid foam formulation usually requires higher hydroxyl number in the range of >200 mg KOH/g. Hydroxyl number analyses of particular examples of liquefied biopolyols showed values in the 200~800 mg KOH/g range, more particularly from about 400-750 mg KOH/g, which is better suited for rigid foam formulation.

Viscosity is considered an important physical property of the polyol. It indicates the degree of oligomerization of the reactants (cellulose and glycerol, among others). In accordance with certain aspects, the viscosity of the polyol composition may fall within a range from about 3,000-10,000 cP. The dynamic viscosities (centipoise, cP measured at 20° C.) of the samples may be determined using a commercially-available rheometer, example—Model RS 100 Rheometer (Haake-Thermoelectron, Newington, N.H.). Higher average molecular weights of the biopolyol can have a significant impact in later PU formulations.

The biopolyols in accordance with one particular example were synthesized using soybean straw as the biomass source, crude glycerin as solvent, and sulfuric acid as catalyst. Soybean straw and sulfuric acid were added at mass ratios of 0.5-15% (based on crude glycerin) and 2-8% (based on crude glycerin), respectively. About 200 grams of crude glycerin (as produced as a byproduct of biodiesel production with only minimal refinement to remove floating soaps, etc) was mixed with soybean straw and sulfuric acid in a 500-mL round-bottom three-necked flask. The mixture was heated to a temperature range of 190° C.-200° C. for 60-90 minutes using the heater-condenser set-up described above. The synthesized biopolyols were characterized for PU foam formulation. Polyols with workable viscosity (~3000-10,000 cP) and acid numbers less than 5 mg KOH/g were used for foaming. A modified foaming procedure was used in preparing a PU foam example. About 60 g of liquefied biopolyol, 0.756 g Polycat® 5, 0.504 g Polycat® 8, 1.5 g DABCO® DC5357 and 1-6% water as blowing agent were added by weighing into a 400-mL disposable paper drinking cup and mixed at high speed with an electric mixer for 15 seconds. The mixture was allowed to degas for 120 seconds after which the A-side component isocyanate PAPI® 27 was rapidly added while continuously stirring for another 10~15 seconds at the same speed. The foam mixture was immediately poured into a wooden mold (11.4 cm×11.4×21.6 cm) lined with aluminum foil and was allowed to rise and set at ambient conditions (23° C.).

Molds in different shapes and dimensions can be used depending on the final use of the PU foams. The proposed bio-based PU can be potentially used for foams, coatings, adhesives, sealants, elastomers and any other typical use for PU. PU foams can be used for insulation, packaging, construction, automotive, furniture, bedding, agricultural film, and door panels, etc. Foams produced in accordance with certain aspects of the present invention are suitable for use in those applications typically used for polyurethane foam. For example, rigid foams can be used in the construction industry and for insulation for appliances, while flexible foams and elastomers can be used in applications such as furniture, mattresses, shoe soles, automobile seats, sun visors, steering wheels, arm rests, door panels, noise insulation parts and dash boards. Foams can be prepared and utilized in various forms, such as molded packing foam, molded insulation boarding, spray-on insulation and spray-in protective foam for packaging.

The PU foam is expected to be biodegradable and would be particularly useful in the production of loose-fill packing material such as packaging peanuts. PU foams produced in accordance with certain aspects of the present invention may be water resistant. The PU foams produced in accordance with certain aspects are considered to be closed cell which means that each cell which makes up the foam structure is completely closed-off to surrounding cells. This prevents water or moisture from entering the cells for short periods of time (up to several months). Long-term exposure to water may soften the polyurethane structure due to its partly biodegradable property.

Tables 2 and 3 below provide a comparison between polyols and PU foams produced in accordance with other methods utilizing bio-based materials and particular examples in accordance with certain embodiments of the process described herein. Notably, the PU foam produced using crude glycerin and biomass exhibits a higher compression strength compared to soy based and solvent based foams. Polyurethane foam produced in accordance with certain aspects may have a compression strength of at least 400 kPa.

TABLE 2

Comparison of specific examples of the proposed technology with other methods:

|  | Soy-base | Solvent-based | Purified Glycerin | Inventive Example |
|---|---|---|---|---|
| Feedstock | Soybean oil | Biomass | Biomass | Biomass |
| Solvents | EG, Glycerin | PEG, EG, DEG | Purified glycerin | Crude glycerin |
| Liquefaction process | No | Yes | Yes | Yes |
| Biomass: solvent/crude glycerin | — | 20%-50% | 20%-50% | 0%-20% |
| Temperature | — | 140-180° C. | ~160° C. | 180-200° C. |
| Catalyst loading | — | ~3% $H_2SO_4$ | 1.0-2.0% $H_2SO_4$ | 2-6% $H_2SO_4$ |
| Time | — | 1-8 h | 1-8 h | 0.5-1.5 h |
| Agitation | — | 400 rpm | — | 100 rpm |

TABLE 3

Comparison of the properties of biopolyols and polyurethane (PU)

|  | Soy-based | Solvent-based | Purified Glycerin | Inventive Example (crude glycerin) |
|---|---|---|---|---|
| Hydroxyl No. (mg KOH/g) | 6.0-200 | 130-648 | 270-310 | 400-750 |
| Compression strength, kPa | 75-380 | 80-280 | — | 40-900 |
| Heat conductivity, W/m ° C. | 0.026-0.044 | — | — | 0.016-0.077 |
| Density, kg/m³ | 30-55 | 33-57 | — | 30-60 |

Having described the invention in detail and by reference to disclosed embodiments thereof, it will be apparent that modifications and variations are possible without departing from the scope of the invention as defined in the following claims:

What is claimed is:
1. A method for producing a polyol comprising:
    combining lignocellulosic biomass with a solvent comprising unrefined crude glycerine to form an admixture, wherein said unrefined crude glycerin is a by-product of a transesterification process for producing biodiesel fuel; and heating the admixture to liquefy the biomass to produce a polyol capable of being reacted with an isocyanate to produce a polyurethane.

2. A method in accordance with claim 1 wherein the solvent comprises at least 90% unrefined crude glycerine by weight based on the total solvent weight.

3. A method in accordance with claim 1 wherein the ratio of biomass to solvent is about 0.5%-15%, wherein the ratio is expressed as a percentage equivalent to the mass of biomass divided by the mass of solvent.

4. A method in accordance with claim 1 wherein the step of heating the admixture comprises heating the admixture to a temperature of 130° C. to 220° C. in the presence of an acid selected from the group consisting of $H_2SO_4$, HCl, and $H_3PO_4$ and results in a biomass conversion of at least 70%.

5. A method in accordance with claim 3 wherein the ratio of biomass to solvent is about 5%-10%.

6. A method in accordance with claim 1 wherein the liquefaction results in a biomass conversion of at least 80%.

7. A method in accordance with claim 1 wherein the polyol is derived from non-petroleum feedstock.

8. A method in accordance with claim 1 wherein the solvent consists essentially of unrefined crude glycerin.

9. A method in accordance with claim 8 wherein the ratio of biomass to solvent is about 0.05%-20% wherein the ratio is expressed as a percentage equivalent to the mass of biomass divided by the mass of solvent.

10. A method in accordance with claim 9 wherein the step of heating the admixture comprises heating the admixture to a temperature of 130° C. to 220° C. and results in a biomass conversion of at least 70%.

11. A method in accordance with claim 1 wherein the ratio of biomass to solvent is about 0.05%-20%, wherein the ratio is expressed as a percentage equivalent to the mass of biomass divided by the mass of solvent.

12. A method in accordance with claim 1 wherein the step of heating the admixture comprises heating the admixture to a temperature of about 180° C. to 220° C. in the presence of an acid selected from the group consisting of $H_2SO_4$, HCl, and $H_3PO_4$ and results in a biomass conversion of at least 70%.

13. A method in accordance with claim 1 wherein the step of heating the admixture comprises heating the admixture to a temperature of about 180° C. to 215° C. in the presence of an acid selected from the group consisting of $H_2SO_4$, HCl, and $H_3PO_4$ and results in a biomass conversion of at least 70%.

14. A polyol composition produced in accordance with the method of claim 1.

15. The polyol composition of claim 14 wherein the polyol has a hydroxyl number of between about 200-800 mg KOH/g.

16. The polyol composition of claim 14 wherein the polyol has an acid number of between about 2-50 mg KOH/g.

17. A method for producing a polyol comprising:
combining lignocellulosic biomass with a solvent consisting essentially of unrefined crude glycerine, wherein the ratio of biomass to solvent is about 0.05%-20%, wherein the ratio is expressed as a percentage equivalent to the mass of biomass divided by the mass of solvent, to form an admixture, wherein said unrefined crude glycerin is a by-product of a transesterification process for producing biodiesel fuel; and heating the admixture to a temperature of 130° C. to 220° C. for an amount of time sufficient to effectively liquefy the biomass resulting in a biomass conversion of at least 70% to produce a polyol wherein said polyol is capable of being reacted with an isocyanate to produce a polyurethane.

18. A method in accordance with claim 17 including an acid in the admixture.

19. A method in accordance with claim 18, wherein the acid is sulfuric acid.

* * * * *